US011726220B2

(12) United States Patent
Marsden

(10) Patent No.: US 11,726,220 B2
(45) Date of Patent: Aug. 15, 2023

(54) RADIATION DETECTORS FOR SCANNING SYSTEMS, AND RELATED SCANNING SYSTEMS

(71) Applicant: Analogic Corporation, Peabody, MA (US)

(72) Inventor: Lane Marsden, Peabody, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 17/152,530

(22) Filed: Jan. 19, 2021

(65) Prior Publication Data

US 2022/0229195 A1  Jul. 21, 2022

(51) Int. Cl.
*G01T 1/29* (2006.01)
*A61B 6/03* (2006.01)
*G01T 1/20* (2006.01)
*A61B 6/00* (2006.01)

(52) U.S. Cl.
CPC .............. *G01T 1/2985* (2013.01); *A61B 6/03* (2013.01); *A61B 6/4488* (2013.01); *G01T 1/2018* (2013.01)

(58) Field of Classification Search
CPC ........................................................ A61B 6/03
See application file for complete search history.

(56) References Cited

U.S. PATENT DOCUMENTS

| | | | |
|---|---|---|---|
| 7,582,879 B2 | 9/2009 | Abenaim et al. | |
| 7,778,381 B2 | 8/2010 | Nishide et al. | |
| 8,525,119 B2 | 9/2013 | Luhta et al. | |
| 8,829,446 B2 | 9/2014 | Abenaim et al. | |
| 8,995,610 B2 | 3/2015 | Ying et al. | |
| 9,513,236 B2 * | 12/2016 | Kawaguchi | A61B 6/032 |
| 10,459,094 B2 | 10/2019 | Simanovsky et al. | |
| 10,488,532 B2 | 11/2019 | Abenaim et al. | |

(Continued)

FOREIGN PATENT DOCUMENTS

| | | | | |
|---|---|---|---|---|
| DE | 102007033463 A1 * | 1/2009 | | A61B 6/4488 |
| JP | H09-508545 A  * | 9/1997 | | A61B 6/03 |
| WO | 2004/072679 A2 | 8/2004 | | |

OTHER PUBLICATIONS

Siemens AG—DE 102007033463 A1—Google Patent English obtained Nov. 18, 2022 (Year: 2022).*

(Continued)

*Primary Examiner* — David P Porta
*Assistant Examiner* — Jeremy S Valentiner
(74) *Attorney, Agent, or Firm* — TraskBritt

(57) ABSTRACT

A radiation scanning system comprises a radiation detector configured to measure at least some radiation. The radiation detector comprises an arc portion exhibiting a semicircular shape, the arc portion comprising a plurality of facets on a side thereof, a detector module coupled to each facet, the detector module comprising a base portion comprising a first substantially planar surface in contact with the facet, a detector unit coupled to a second substantially planar surface of the base portion, the second substantially planar surface parallel with the first substantially planar surface, and a cooling structure in thermal communication with a side of the arc portion opposite the plurality of facets. Related radiation detectors and radiation systems are also disclosed.

23 Claims, 11 Drawing Sheets

(56) References Cited

U.S. PATENT DOCUMENTS

| | | |
|---|---|---|
| 2005/0117698 A1* | 6/2005 | Lacey .................. A61B 6/4488 378/19 |
| 2007/0007455 A1 | 1/2007 | Juni |
| 2007/0280410 A1 | 12/2007 | Lutz et al. |
| 2008/0080666 A1 | 4/2008 | Carmi |
| 2008/0205586 A1* | 8/2008 | Nambu ................. G01T 1/1647 378/19 |
| 2012/0069954 A1* | 3/2012 | Iso ........................ A61B 6/03 378/7 |
| 2012/0243661 A1* | 9/2012 | Guo ..................... A61B 6/4488 378/19 |
| 2013/0134313 A1 | 5/2013 | Niederlöhner et al. |
| 2013/0221468 A1 | 8/2013 | Bolognia |
| 2014/0010426 A1* | 1/2014 | Basu ..................... G06T 11/005 382/131 |
| 2014/0138553 A1* | 5/2014 | Ogawa .................. G01T 1/17 250/393 |
| 2015/0319830 A1 | 11/2015 | Lacey |
| 2016/0154124 A1 | 6/2016 | Luhta et al. |
| 2018/0095182 A1* | 4/2018 | Su ......................... A61B 6/037 |
| 2019/0235099 A1 | 8/2019 | Luhta et al. |
| 2020/0000422 A1* | 1/2020 | Yu ......................... A61B 6/032 |
| 2020/0046306 A1 | 2/2020 | Marsden et al. |
| 2021/0038175 A1* | 2/2021 | Linev .................. A61B 6/5235 |
| 2021/0215838 A1* | 7/2021 | Ye ....................... A61B 6/4488 |
| 2021/0219930 A1* | 7/2021 | Tsuchiya ............... A61B 6/032 |

OTHER PUBLICATIONS

Analogic Corp.—JP H09-508545 A—PE2E Search English obtained Nov. 17, 2022 (Year: 2022).*
International Search Report for International Application No. PCT/US2021/013991, dated Oct. 14, 2021, 6 pages.
International Written Opinion for International Application No. PCT/US2021/013991, dated Oct. 14, 2021, 11 pages.

* cited by examiner

RADIATION DETECTORS FOR SCANNING SYSTEMS, AND RELATED SCANNING SYSTEMS

FIELD

Embodiments of the disclosure relate generally to radiation detectors for scanning systems. More particularly, embodiments of the disclosure relate to a radiation detector including an arc portion having a first side configured to carry detector modules for detecting impinging radiation and a second side in thermal communication with one or more heat transfer apparatuses for maintaining a temperature of the detector modules.

BACKGROUND

Radiation imaging modalities such as computed tomography (CT) systems and single-photon emission computed tomography (SPECT) systems, and/or positron emission tomography (PET), for example, are useful to provide information, or images, of interior aspects of an object under examination. In transmission imaging modalities, such as CT, the object is exposed to radiation comprising photons (e.g., such as x-rays, gamma rays, without limitation), and an image(s) is formed based upon the radiation absorbed and/or attenuated by the interior aspects of the object, or rather a number of radiation photons that are able to pass through the object. Generally, highly dense aspects of the object absorb and/or attenuate more radiation than less dense aspects, and thus an aspect having a higher density, such as a bone or metal, for example, will be apparent when surrounded by less dense aspects, such as muscle or clothing. Emission imaging modalities such as SPECT and PET form image(s) based on the radiation emitted from a radioactive tracer that provides functional information of an object.

Radiation photons that pass through an object impinge a surface of one or more detector elements of a detector array (logically referred to as "detector cells") that typically directly or indirectly generate electrical charge in response to the impinging radiation photons. The detector array typically comprises a plurality of detector cells, respectively configured to convert detected radiation into electrical signals. A magnitude of attenuation by an object in an examination region is inversely related to an amount or rate of electrical charge generated by a detector element. Based upon the number of radiation photons detected by respective detector cells and/or the electrical charge generated by respective detector cells between samplings, images can be reconstructed that are indicative of the density, z-effective (also referred to as the effective atomic number), shape, and/or other properties of the object and/or aspects thereof.

The number of detector cells within a detector array may be application specific. For example, in some computed tomography applications, a number of typical detector cells may range from about 16,000 to about 320,000 depending on the desired degree of coverage of the computed tomography system.

In use and operation, typical detector cells and the electronic boards associated with such detector cells known to the inventors of this disclosure, generate heat. Detector cells and detector cell arrangements of conventional detector arrays are typically individually cooled by airflow and are susceptible to temperature changes caused by changes in airflow when a radiation scanner changes rotational speed. Inadequate temperature control of detector cells may, for example, contribute to artifact and other noise in images generated by a radiation imaging system. In addition, due to the rotation of the radiation imaging system, conventional detector cells are subject to significant mechanical stresses during use and operation and suffer from bending or other deflection. The bending and deflection of the detector cells may reduce the quality and accuracy of the images created by the radiation imaging system. Other disadvantages of typical detector cells known to the inventors of this disclosure include the difficulty of placement and alignment of detector cells, and access for replacement of detector cells when one or more detector cells fails.

DETAILED DESCRIPTION

Figure 1:
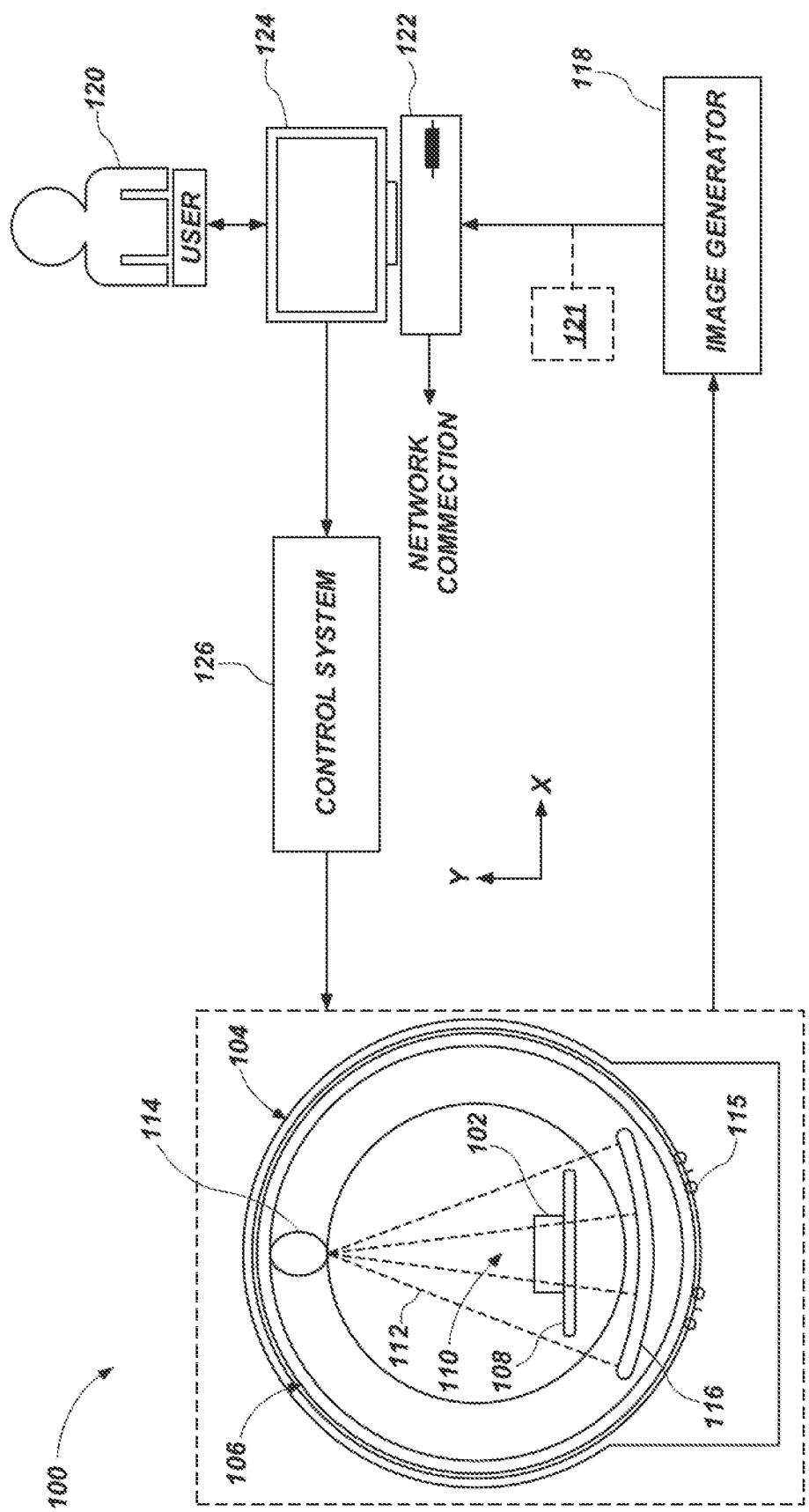
FIG. 1 is a schematic of a scanning system to perform transmission radiation-based scanning, in accordance with embodiments of the disclosure.

The illustrations presented in this disclosure are not meant to be actual views of any particular scanning system for performing radiation-based (e.g., computed tomography (CT)) scanning or component thereof or component thereof, but are merely idealized representations employed to describe illustrative embodiments. Thus, the drawings are not necessarily to scale.

The following description provides specific details, such as material types, dimensions, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional fabrication techniques employed in the industry. In addition, the description provided below does not form a complete apparatus or system for a scanning system including a detector array comprising a cradle. Only those process acts and structures necessary to understand the embodiments of the disclosure are described in detail below. Also note, any drawings accompanying the present application are for illustrative purposes only, and are thus not drawn to scale. Additionally, elements common between figures may retain the same numerical designation.

Disclosed embodiments relate generally to scanning systems configured to inspect translated objects using radiation-based scanning that may reduce artifact and other noise in images generated with the scanning systems. More specifically, disclosed are embodiments of scanning systems configured to control a temperature of detector modules of the radiation detector of the scanning system and provide structural support to the detector modules during use and operation, reducing the artifact in the generated images. In addition, the scanning systems disclosed herein may facilitate placement of the detector modules at precise locations and aligned with respect to other components of the scanning system, and serviceability of the scanning systems (e.g., by facilitate replacement of the detector modules).

Terms used in the present disclosure and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.). As used herein, "each" means some or a totality. As used herein, "each and every" means a totality.

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

As used herein, the terms "substantially" and "about" in reference to a given parameter, property, or condition means and includes to a degree that one of ordinary skill in the art would understand that the given parameter, property, or condition is met with a degree of variance, such as within acceptable manufacturing tolerances. For example, a parameter that is substantially and/or about a specified value may be at least about 90% the specified value, at least about 95% the specified value, at least about 99% the specified value, or even at least about 99.9% the specified value.

As used herein, spatially relative terms, such as "upper," "lower," "bottom," and "top," are for ease of description in identifying one element's relationship to another element, as illustrated in the figures. Unless otherwise specified, the spatially relative terms are intended to encompass different orientations of the materials in addition to the orientation depicted in the figures. Thus, the term "upper" can encompass elements above, below, to the left of, or to the right of other elements, depending on the orientation of a device. The materials may be otherwise oriented (rotated ninety degrees, inverted, without limitation) and the spatially relative descriptors used herein interpreted accordingly.

In this description the term "coupled" and derivatives thereof may be used to indicate that two elements co-operate or interact with each other. When an element is described as being "coupled" to another element, then the elements may be in direct physical or electrical contact or there may be intervening elements or layers present. In contrast, when an element is described as being "directly coupled" to another element, then there are no intervening elements or layers present. The terms "on" and "connected" may be used in this description interchangeably with the term "coupled," and have the same meaning unless expressly indicated otherwise or the context would indicate otherwise to a person having ordinary skill in the art.

As used herein, "arc" means a circular arc, or a portion of a circular arc.

According to embodiments described herein, a scanning system (e.g., an imaging system, a radiation imaging system, a radiation scanning system) comprises a gantry including a radiation source and a radiation detector including a detector array configured to observe (e.g., measure, detect, without limitation) radiation photon impingent thereon that passes through an object located in an examination region defined between the radiation source and the radiation detector. A radiation detector comprises a detector array comprising a support structure configured to be operably coupled to the gantry. A support structure may include an arc portion configured to carry a plurality of detector modules. An arc portion may be sized and shaped to span substantially an entire length of a support structure and a detector array carried thereby. The arc portion may include a plurality of facets, each facet including a surface and arranged such that the respective surface is oriented at a substantially perpendicular angle with respect to a radiation path of at least some incident radiation (e.g., an imaginary line between the radiation source and the surface of the facet, without limitation). Each facet may be coupled with a detector module including one or more detector units (e.g., detector tiles, without limitation) at a surface of each respective facet, the surface of each facet facing inward toward the radiation source. In other words, each facet may include a surface that is oriented toward the radiation source to receive radiation from the radiation source at about a 90 degree angle of incidence. The surface of each facet may be configured to receive a detector unit. A detector module may include a base structure on which one or more detector units are supported. A detector module (e.g., a base structure of the detector module) may be substantially completely supported by a facet. Stated another way, substantially all of a surface of a single detector module may contact a surface of a single one of the facets such that substantially no portion of a surface of a detector module in contact with a facet is unsupported by the facet (e.g., the detector module does not include unsupported portions that span between different portions of the facet without contacting the surface of the facet, without limitation). Since substantially all of a disclosed detector module is supported by a facet, during operation of a radiation system (e.g., rotation of the gantry, without limitation), detector modules may be subject to no or inconsequential deflection or bending as in conventional detector modules and radiation systems, improving noise and/or artifact immunity (e.g., limiting noise or artifacts that may be caused by deflection or bending, without limitation) in images generated by a scanning system and improving the quality of the generated images. In addition, the detector modules disclosed herein may be more easily accessed and replaced due to the position of the detector modules on the facets of the arc portion, as compared to replacement of detector modules of conventional scanning systems that may be mounted, for example, to a support structure at an angle, such as at 90°.

According to embodiments disclosed herein, detector modules may be in direct thermal contact with the facets. The facets may form a portion of an arc portion and may be located on a first side of the arc portion. The arc portion may define a thermal mass extending substantially an entire length of the support structure carrying the detector modules. One or more heater elements may be in thermal communication with a second side of the arc portion and configured to maintain a temperature of the arc portion at a desired temperature. In addition, a second side of the arc portion may be in thermal communication with one or more heat exchangers for removing heat from the arc portion. In some embodiments, the heat exchanger comprises cooling elements, such as one or more of cooling fins, a water cooler, or a chiller. In operation, a temperature exhibited by the detector modules may be controlled indirectly through the arc portion, such as by contact of second side of the arc portion with heat exchanger. As a non-limiting example, a temperature of detector modules may be controlled through the arc portion, rather than being heated or cooled directed by the respective heater elements or cooling elements. Controlling the temperature of the detector modules through the arc portion may reduce temperature swings in the detector modules and increase a time constant of temperature change of the detector modules relative to conventional scanning systems which are cooled by the passage of air during rotation of the rotor and the detector modules during operation. Stated another way, a rate of temperature change of detector modules coupled to the arc portion during operation of the scanning system may be substantially less than of detector modules of conventional scanning systems. Increased temperature stability of the detector modules of the scanning system may reduce measurement error attributable to temperature changes and improve quality of images generated from the scanning system.

FIG. 1 is a schematic of a scanning system 100 to perform transmission radiation-based (e.g., CT) scanning, in accordance with embodiments of the disclosure. Techniques in accordance with this disclosure may find applicability with, for example, CT systems, diffraction systems, and/or other systems comprising a radiation detector system. The scanning system 100 may be configured to examine one or more objects 102 (e.g., a human subject, a series of suitcases at an airport, freight, parcels, without limitation). The scanning system 100 may include, for example, a stator 104 and a rotor 106 rotatable relative to the stator 104. During examination, the object(s) 102 may be located on a support 108, such as, for example, a bed, roller conveyor, or conveyor belt, that is selectively positioned in an examination region 110 (e.g., a hollow bore in the rotor 106 in which the object(s) 102 is exposed to radiation 112), and the rotor 106 may be rotated about the object(s) 102 by a motivator 115 (e.g., motor, drive shaft, chain, without limitation).

The rotor 106 may surround a portion of the examination region 110 and may be configured as, for example, a gantry supporting at least one radiation source 114 (e.g., an ionizing x-ray source, gamma-ray source, without limitation), the at least one radiation source 114 oriented to emit radiation toward the examination region 110 and at least one radiation detector 116 supported on a substantially diametrically opposite side of the examination region 110 (which may also be a substantially diametrically opposite side of rotor 106) relative to the radiation source(s) 114. During a contemplated examination of object(s) 102 by the scanning system 100, the radiation source(s) 114 emits fan and/or cone shaped radiation 112 configurations toward the examination region 110. The radiation 112 may be emitted, for example at least substantially continuously or intermittently (e.g., a pulse of radiation 112 followed by a resting period during which the radiation source(s) 114 is not activated).

As the emitted radiation 112 traverses the examination region 110 and the object(s) 102, the radiation 112 may be attenuated differently by different aspects of the object(s) 102. Because different aspects attenuate different amounts (e.g., percentages, without limitation) of the radiation 112, an image or images can be generated based upon the attenuation, or variations in the number of radiation photons that are detected by the radiation detector 116. As non-limiting examples, more dense aspects of the object(s) 102, such as an inorganic material, may attenuate more of the radiation 112 (e.g., causing fewer photons to be detected by the radiation detector 116) than less dense aspects, such as organic materials.

The radiation detector 116 may include, for example, many individual detector elements arranged in a pattern (e.g., a row or an array) on one or more detection assemblies (also referred to as detection modules, detector modules, and/or the like), which are operatively connected to one another to form the radiation detector 116. In some embodiments, the detector elements may be configured to indirectly convert (e.g., using a scintillator array and photodetectors) detected radiation into analog signals. In other embodiments, the detector elements are configured to directly convert the detected radiation into analog signals. Further, the radiation detector 116, or detection assemblies thereof, may include electronic circuitry, such as, for example, an analog-to-digital (A/D) converter, configured to filter the analog signals, digitize the analog signals, and/or otherwise process the analog signals and/or digital signals generated thereby. Digital signals output from the electronic circuitry may be conveyed from the radiation detector 116 to digital processing components configured to store data associated with the digital signals and/or further process the digital signals.

In some embodiments, the digital signals may be transmitted to an image generator 118 configured to generate image space data, also referred to as images, from the digital signals using a suitable analytical, iterative, and/or other reconstruction technique (e.g., backprojection reconstruction, tomosynthesis reconstruction, iterative reconstruction, without limitation). In this way, the data may be converted from projection space to image space, a domain that may be more understandable by a user 120 viewing the image(s), for example. Such image space data may depict a two dimensional representation of the object(s) 102 and/or a three dimensional representation of the object(s) 102. In other embodiments, the digital signals may be transmitted to other digital processing components, such as a threat analysis component 121, for processing.

The illustrated scanning system 100 may also include a terminal 122 (e.g., a workstation or other computing device), configured to receive the image(s), which can be displayed on a monitor 124 to the user 120 (e.g., security personnel, medical personnel, without limitation). In this way, the user 120 can inspect the image(s) to identify areas of interest within the object(s) 102. The terminal 122 may also be configured to receive user input which may direct operations of the scanning system 100 (e.g., a rate at which the support 108 moves, activation of the radiation source(s) 114, without limitation) and connected to additional terminals 122 through a network (e.g., a local area network or the Internet, without limitation).

A control system 126 may be coupled (e.g., operably coupled) to the terminal 122. The control system 126 may be configured to automatically control at least some operations of the scanning system 100. For example, the control system 126 may be configured to directly and/or indirectly, automatically, and dynamically control the rate at which the support 108 moves through the examination region 110, the rate at which the rotor 106 rotates relative to the stator 104, activation, deactivation, and output level of (e.g., intensity of radiation emitted by) the radiation source(s) 114, or any combination or subcombination of these and/or other operating parameters. In some embodiments, the control system 126 may also accept manual override instructions from the terminal 122 and to issue instructions to the scanning system 100 to alter the operating parameters of the scanning system 100 based on the manual override instructions. The control system 126 may be located proximate to a remainder of the scanning system 100 (e.g., integrated into the same housing or within the same room as the remaining components) or may be distal from the scanning system 100 (e.g., located in another room, such as, for example, an on-site control room, an off-site server location, a cloud storage system). The control system 126 may be dedicated to control a single scanning system 100, or may control multiple scanning systems 100 in an operative grouping or subgrouping.

Figure 2A:
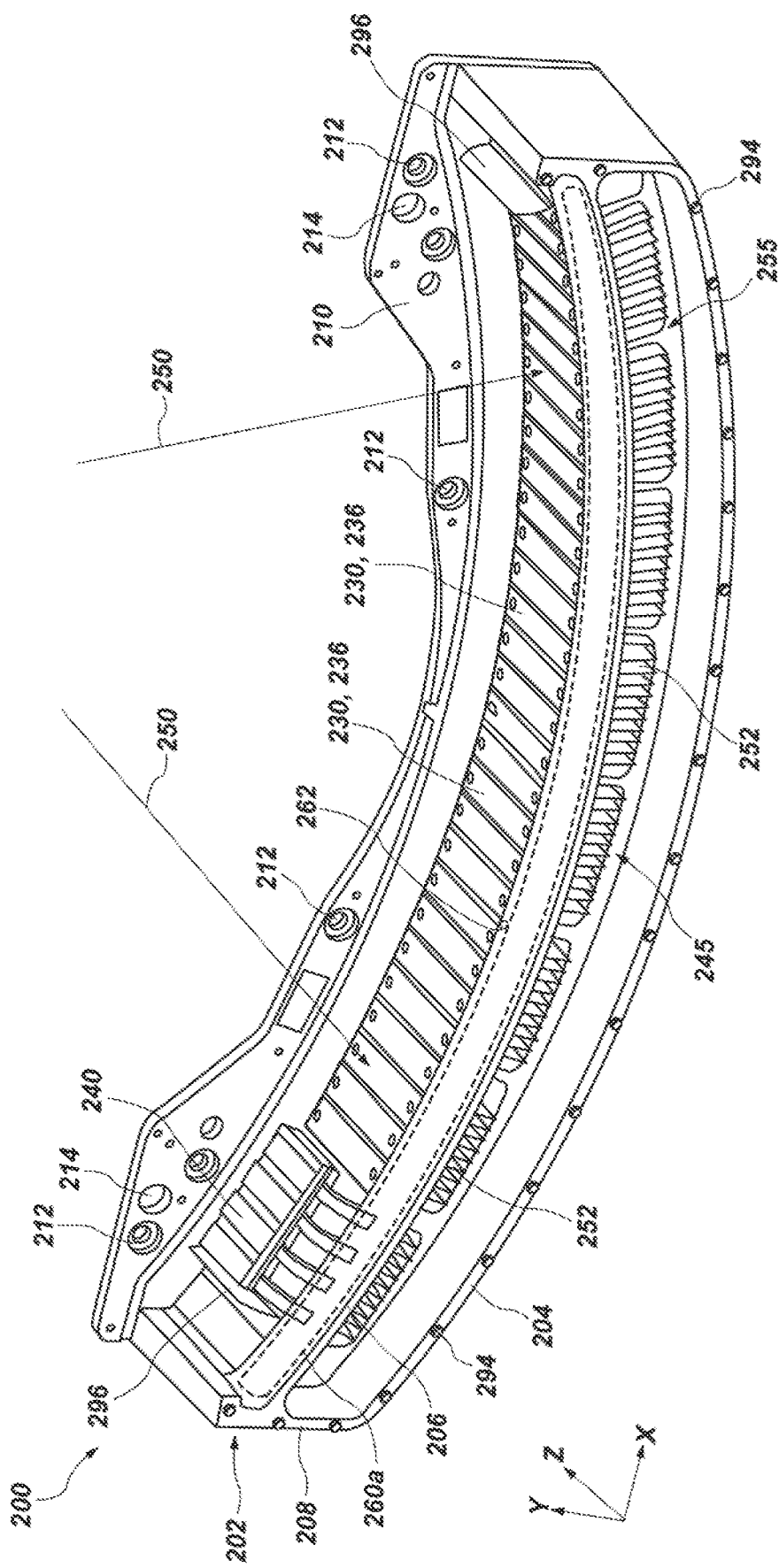
FIG. 2A is a simplified perspective view of a radiation detector, in accordance with embodiments of the disclosure.
Figure 2B:
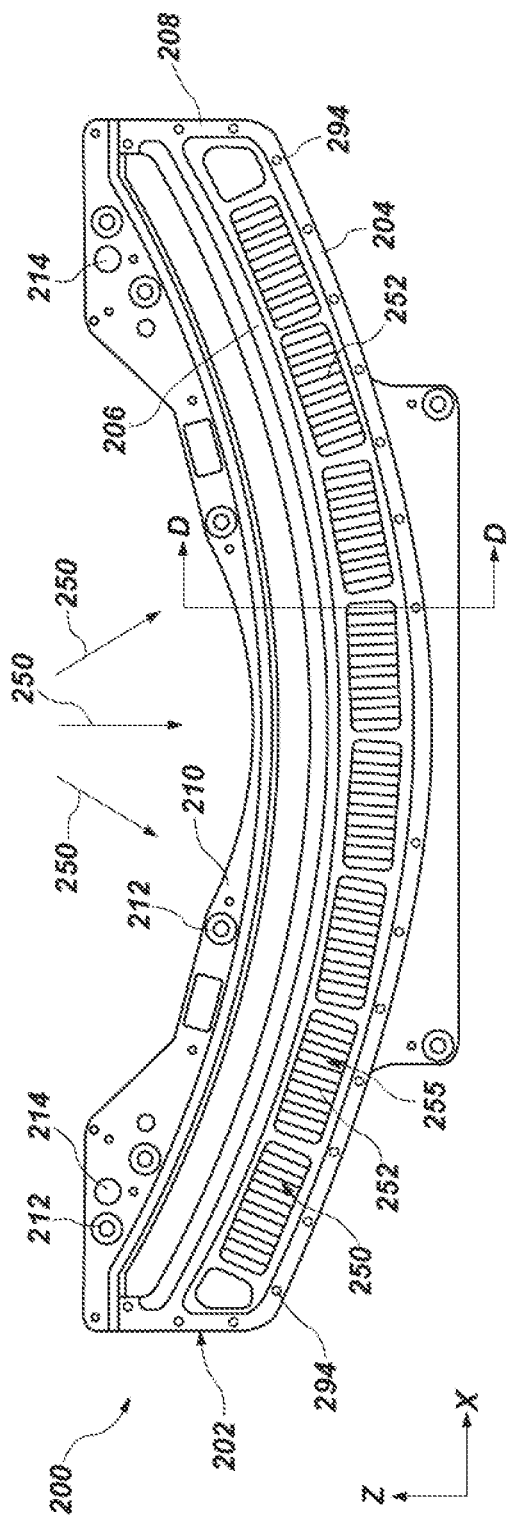
FIG. 2B is a simplified front view of the radiation detector of FIG. 2A.
Figure 2C:
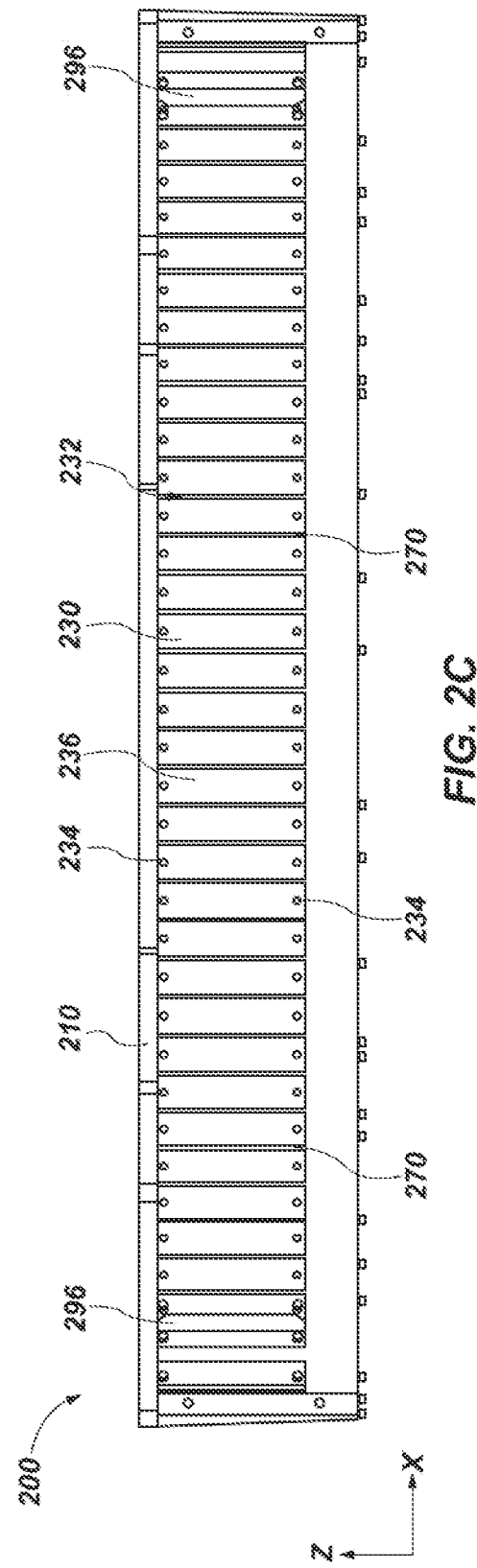
FIG. 2C is a simplified top view of the radiation detector of FIG. 2A.
Figure 2D:
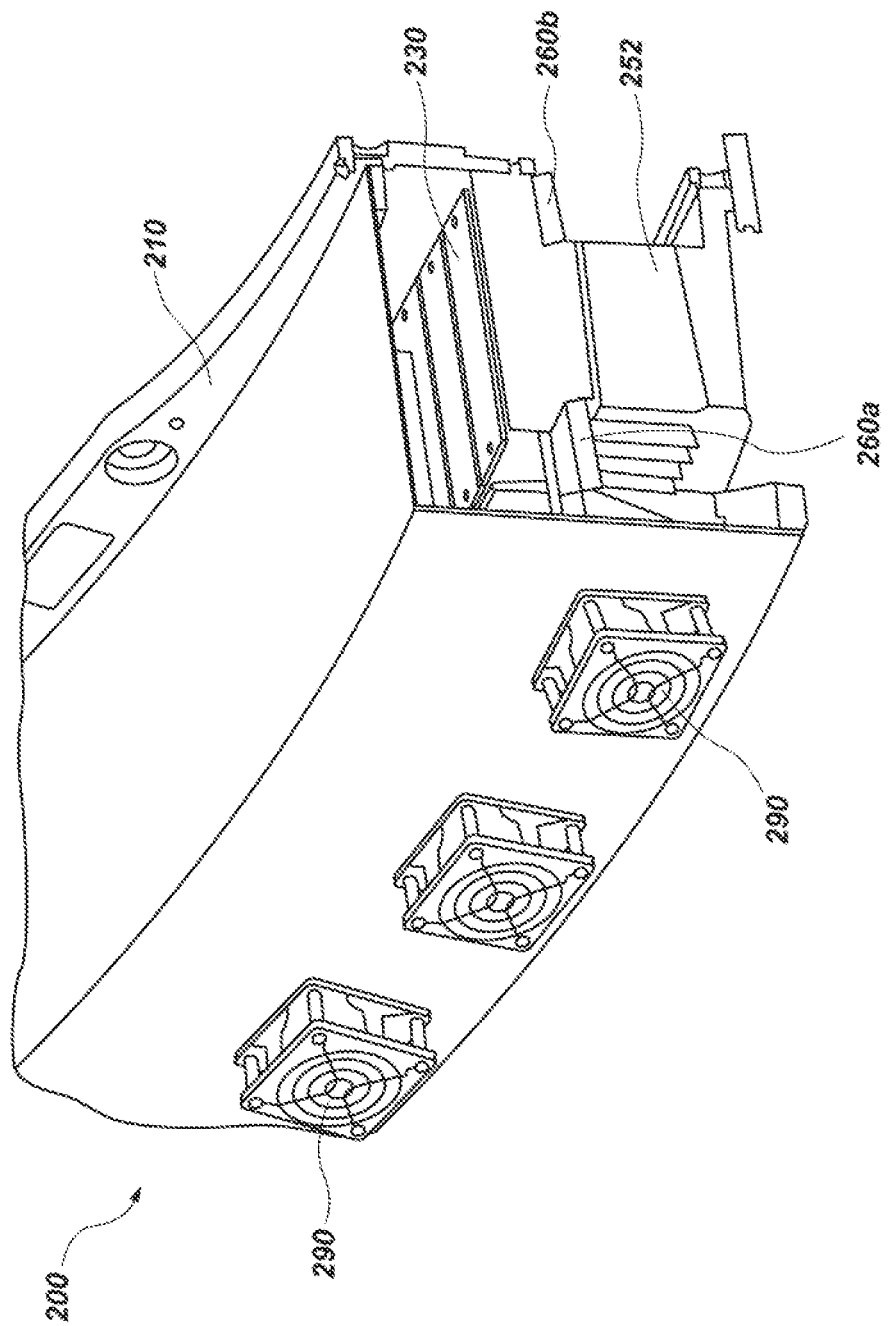
FIG. 2D is a simplified cross-sectional view of the radiation detector taken through section line D-D of FIG. 2B.
Figure 2E:
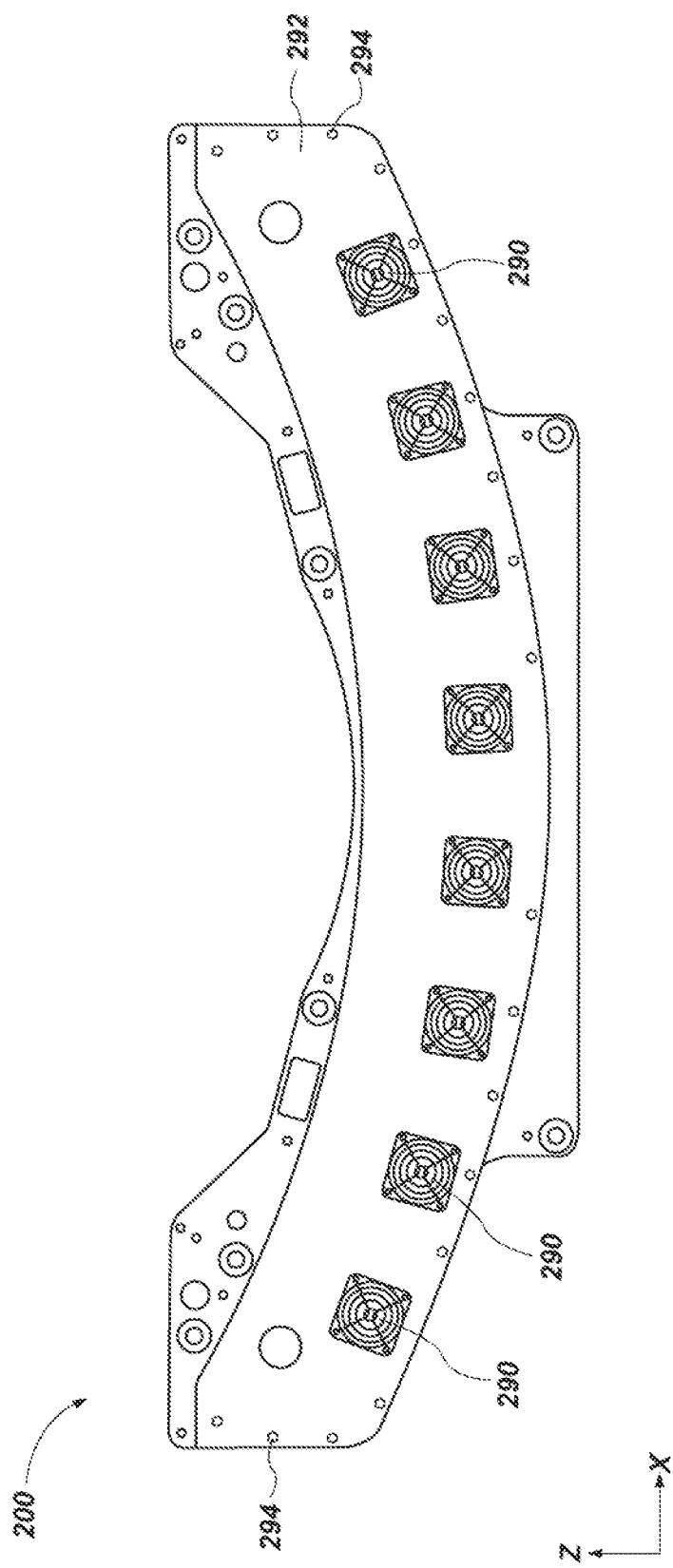
FIG. 2E is a simplified front view of the radiation detector of FIG. 2A including a front cover.
Figure 2F:
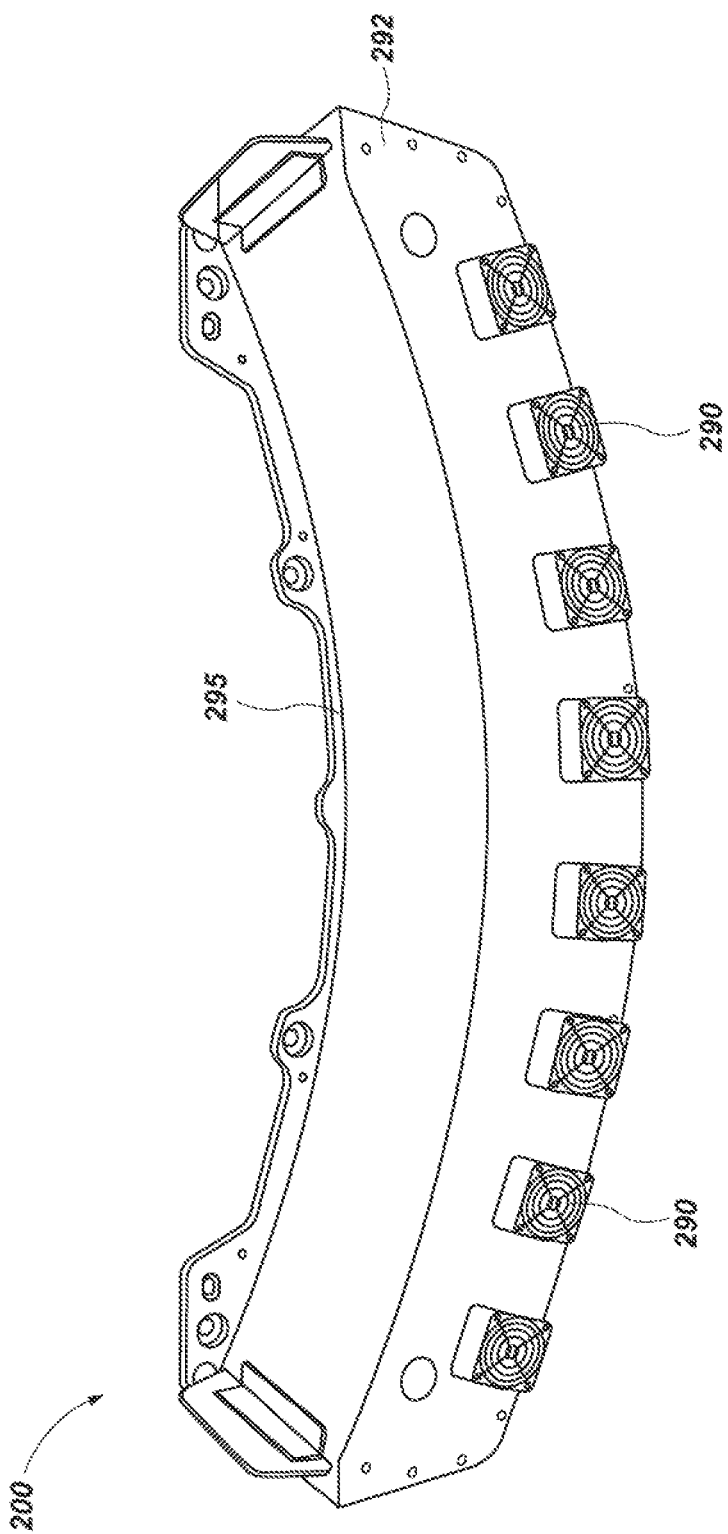
FIG. 2F is a simplified perspective view of the radiation detector of FIG. 2A including a top cover.

FIG. 2A is a simplified perspective view of a radiation detector 200, in accordance with embodiments of the disclosure. As a non-limiting example, the radiation detector 200 may form a totality or a portion of the radiation detector 116 of FIG. 1. FIG. 2B is a simplified front view of the radiation detector 200, FIG. 2C is a simplified top view of the radiation detector 200, and FIG. 2D is a simplified cross-sectional view of the radiation detector 200 taken through section line D-D of FIG. 2B. FIG. 2E is a simplified front view of the radiation detector 200 with a front cover attached to a support structure thereof, and FIG. 2F is a simplified perspective view of the radiation detector 200 with top cover over a detector array thereof, in accordance with embodiments of the disclosure. The radiation detector 200 may also be referred to herein as a "detector measurement system" (DMS).

With reference to FIG. 2A through FIG. 2D, the radiation detector 200 may include a support structure 202 (which may also be referred to herein as a "saddle," a "cradle," or a "frame") including a base portion 204, and an arc portion 206 vertically above the base portion 204 and connected to the base portion 204 by sidewalls 208.

Each of the base portion 204, the arc portion 206, and the sidewalls 208 may include a unitary body or element. Stated another way, the base portion 204, the arc portion 206, and the sidewalls 208 may form an integral member. In other words, in some such embodiments, the base portion 204, the arc portion 206, and the sidewalls 208 form a continuous structure. In some embodiments, the base portion 204, the arc portion 206, and the sidewalls 208 are formed of and include the same material composition. In some embodiments, the support structure 202 comprises a metal exhibiting a relatively low density (as compared to other metals), such as, for example, aluminum. However, the disclosure is not so limited and the support structure 202 may include a different material composition than that described above. In addition, non-unitary bodies or elements forming the structure of the support structure 202 do not exceed the scope of this disclosure, such as, as a non-limiting example, portions that are coupled using any suitable technique. In some embodiments, the support structure 202 (e.g., the base portion 204, the arc portion 206, and the sidewalls 208) comprises a material exhibiting shielding properties with respect to the incident radiation 250. By way of non-limiting example, in some embodiments, the support structure 202 comprises tungsten.

The support structure 202 may exhibit a generally arcuate shape, such as a circular shape. In some embodiments, the arc portion 206 exhibits a substantially circular shape, such as a truncated circular shape. In other words, the arc portion 206 may exhibit a substantially circular shape, but may not define an entire circle. In some embodiments, a center of the circular shape of the support structure 202 (and the arc portion 206) may correspond to the focal spot of radiation (e.g., to the radiation source 114 (FIG. 1)). Stated another way, the radiation source 114 may be located at the center of a circular shape, a portion of which is defined by the support structure 202 including the arc portion 206. As will be described herein, in other embodiments, the support structure 202 exhibits a different shape, such as a hexagonal or partial-hexagonal shape; a portion exhibiting a truncated circular shape and other portions comprising a linear shape; or a U-shaped structure.

The arc portion 206 may extend substantially along an entire length (e.g., in the X-direction) of the support structure 202. For example, the arc portion 206 may extend from one sidewall 208 to another sidewall 208 along the length of the support structure 202. As will be described herein, the arc portion 206 may be configured to carry detector modules 240 of radiation detector 200.

The radiation detector 200 may include a back plate 210 configured to be removably attached to support structure 202. In the specific non-limiting example depicted by FIG. 2A, the back plate 210 may include apertures 212 configured to receive one or more fasteners for coupling the back plate 210 of the radiation detector 200 to the rotor 106 (FIG. 1). The fasteners may include, as non-limiting examples, bolts, screws, or other structures configured for attaching (e.g., securing) the back plate 210 to the rotor 106. Accordingly, in some embodiments, the back plate 210 is an attachment element and configured to interface the support structure 202 of the radiation detector 200 to the rotor 106. In other words, the back plate 210 may include physical features, such as alignment elements, to facilitate suitable attachment of the radiation detector 200 to the rotor 106. Alignment elements may include, as non-limiting examples, visual alignment elements to assist a user with appropriate orientation and alignment of the back plate 210, the support structure 202, and the rotor 106, and matingly compatible alignment elements to facilitate an appropriate orientation and alignment. In some embodiments, the back plate 210 further comprises additional apertures 214 configured to facilitate alignment of the back plate 210 to the rotor 106.

In some embodiments, the radiation detector 200 may include a base structure configured to be removably attached to the support structure 202, such as to the base portion 204. The base structure may include a surface for receiving one or more electronic boards. As used herein, the term "electronic boards" means electronics, and includes without limitation: integrated circuits (ICs), application specific integrated circuits, digital logic circuits, microcontrollers, microprocessors, and combinations thereof. Electronics of electronic boards may include a number of functional blocks for performing disclosed embodiments or portions thereof coupled by any suitable interconnect, such as a printed circuit board, flexible circuit, a wiring harness, and combinations thereof, without limitation.

The arc portion 206 may include facets 230 configured to receive one of the detector modules 240, as will be described herein. Each facet 230 may be configured to be coupled to a detector module 240. For clarity and ease of understanding, FIG. 2A illustrates only four facets 230 coupled to four respective detector modules 240. However, it will be understood that a detector module 240 may be coupled to each of the facets 230.

Facets 230 may be located on an upper (e.g., a first) surface of the arc portion 206 and may be separated from each other by spaces 232 (FIG. 2C). The upper surface of the arc portion 206 including the facets 230 may be oriented such that the facets 230 face a center of a circle at least partially defined by the support structure 202 including the arc portion 206.

Although FIG. 2A through FIG. 2D illustrate a particular number (in the specific non-limiting example depicted, 36) of facets 230, additional or fewer facets 230 do not exceed the scope of this disclosure. In some embodiments, the arc portion 206 comprises fewer facets 230 (e.g., fewer than 30 facets 230, fewer than 26 facets 230, fewer than 22 facets 230, fewer than 18 facets 230, or fewer than 16 facets 230). In other embodiments, the support structure 202 comprises a greater number of the facets 230 (e.g., greater than 40 facets 230, greater than 50 facets 230, or even greater than 60 facets 230).

Each facet 230 may individually include apertures 234 (FIG. 2C) configured for attachment of a detector module 240 to a respective facet 230. The facets 230 may each include a surface 236 configured to be coupled to (e.g., receive) a complimentary (e.g., corresponding, without limitation) surface of a corresponding detector module 240. In one or more embodiments, the surface 236 may be substantially planar, but a non-planar surface 236 does not exceed the scope of this disclosure. In some embodiments, the surface 236 of each facet 230 is oriented such that a center thereof is oriented at substantially a right angle to intended radiation 250 from the radiation source 114 (FIG. 1). In some embodiments, the surfaces 236 may be oriented such that the surfaces 236 are substantially perpendicular to a path of the radiation 250 emitted from the radiation source 114. In other words, the surfaces 236 may be oriented such that they are substantially perpendicular to a line extending from the respective surface 236 to a center of a circle at least partially defined by the arc portion 206 of the support structure 202. In some embodiments, the surfaces 236 may be oriented with respect to a radiation source such that an angle of incidence of at least some radiation photons impinging the surface 236 is substantially 90 degrees. In some cases, surfaces of the detector modules 240 mounted to the facets 230 are oriented at a right angle to an imaginary line projected from a radiation source (in some cases using a specific location along a path traveled by radiation emitted from a radiation source during an examination, without limitation) to a facet of interest.

The surfaces 236 may be sized and shaped to receive and contact substantially all of or a portion of a surface of a corresponding detector module 240 to provide structural support to the detector modules 240 during use and operation of the scanning system 100 (FIG. 1) (e.g., rotation of the rotor 106 (FIG. 1)). When coupled to the surfaces 236, the detector modules 240 may be oriented to face a direction of the radiation 250 from the radiation source 114 (FIG. 1). The surfaces 236 of the facets 230 may facilitate improved accuracy of desired placement of the detector modules 240 compared to conventional detector arrays that do not include the facets 230 or the arc portion 206. By way of non-limiting example, conventional detector arrays known to inventors of this disclosure may include detector modules that are mounted to a detector array support structure (e.g., cradle) with mounting brackets or blocks including a major surface that mounts to the detector array support structure oriented at an angle (e.g., a right angle) with respect to a surface of the mounting bracket that is configured to receive the detector module. Such a configuration typically requires fabrication of accurate surfaces that are oriented at right angles to each other and which increases the likelihood of misalignment of a detector module to a detector array support structure and the cost of fabrication/assembly. In addition, as will be described herein, the apertures 234 of the facets 230 facilitates serviceability of the radiation detector 200, such as installation and removal of the detector modules 240 from the surfaces 236 of the facets 230 compared to installation and replacement of detector modules of conventional scanning systems.

The detector modules 240 may be configured to generate imaging signals indicative of attenuation of the radiation 250 that impinges the detector module 240. More specifically, the detector modules 240 may be configured to indirectly convert (or directly convert detected radiation 250 into analog or digital imaging signals. For example, the detector modules 240 configured to indirectly convert radiation (e.g., the radiation 250, without limitation) to imaging signals may include a scintillator sub-assembly and a detector sub-assembly, as will be described herein. As a non-limiting example, the detector modules 240 configured to directly convert radiation (e.g., the radiation 250, without limitation), may include a material and/or circuitry adapted to generate an electrical charge or a representation thereof in response to radiation and analog or digital signals indicative of the radiation. In some such embodiments, the detector modules 240 may include a detector sub-assembly comprising, for example, cadmium zinc telluride (CZT) or another direct conversion material, without limitation.

The sidewalls 208 and the arc portion 206 of the support structure 202 may define a cavity 255 configured to at least partially receive one or more heat exchangers 245 (e.g., cooling structures) configured to thermally couple to the arc portion 206 to provide cooling of the detector modules 240 through the arc portion 206. In some embodiments, the heat exchangers comprise fins 252 (e.g., cooling fins) configured to exchange thermal energy with an ambient environment by passing fluid (e.g., air) across (e.g., adjacent to) the fins 252. Stated another way, and as will be described herein, the cavity 255 may be configured to be fluidly coupled to a fluid for exchanging heat with the fins 252. The cavity 255 may be at least partially defined by a lower surface (e.g., a second surface) of the arc portion 206. In some embodiments, the cavity 255 is sized and shaped to facilitate flow of air through the cavity 255 and the fins 252 to transfer heat from the arc portion 206 through the fins 252. The cavity 255 may be in operable communication with fans 290 (FIG. 2D, FIG. 2E, FIG. 2F) configured to provide air to the cavity 255 to facilitate heat transfer from the fins 252.

The fins 252 may include a metal, such as, for example, copper, aluminum, or another material. In some embodiments, the fins 252 comprise the same material composition as the support structure 202. In some embodiments, the fins 252 comprise aluminum (e.g., an aluminum-containing material). In some embodiments, the fins 252 comprise a different material composition than the support structure 202. In some embodiments, the fins 252 are integral with the support structure 202 and extend from, for example, surfaces of the base portion 204 to a lower surface of the arc portion 206. In other embodiments, the fins 252 are configured to be removably coupled to the support structure 202. For example, fins 252 may be detachable from within the cavity 255 and removed from the support structure 202.

The fins 252 may be in direct thermal and physical contact with at least a portion of the arc portion 206. In some embodiments, the fins 252 directly contact the lower surface of the arc portion 206. As described above, the arc portion 206 may be configured to facilitate thermal transfer (e.g., heat transfer) between the detector modules 240 and an external environment (e.g., air circulated through the fins 252). The fins 252 may be sized, shaped, and spaced to facilitate a desired amount of thermal transfer (e.g., heat transfer) from the arc portion 206 to the external environment.

With reference to FIG. 2A and FIG. 2D, the radiation detector 200 may further include one or more heater elements configured to provide heat to the arc portion 206. For example, a front of the radiation detector 200 may include a heater element 260a (FIG. 2A, FIG. 2D) and a back of the radiation detector 200 may include a heater element 260b (FIG. 2D), collectively referred to herein as heater elements 260. The heater element 260a in FIG. 2A is illustrated in broken lines to indicate that the heater element is located under the arc portion 206 (e.g., between the arc portion 206 and the fins 252). In some embodiments, heat from the heater elements 260 is transferred to the detector modules 240 through the arc portion 206 through the respective facets 230. In some embodiments, the heater elements 260 may be configured to maintain the temperature of the arc portion 206 at a substantially uniform temperature. In some embodiments, the heater elements 260 are configured to maintain a temperature of the facets 230 and the detector modules 240 at a temperature above room temperature (e.g., above about 20° C., above about 25° C.).

The heater elements 260 may be located, for example, in front of and behind (e.g., in the Z-direction) facets 230. For example, the heater element 260a may be located in front of the facets 230 and the heater element 260b may be located behind the facets 230. In some embodiments, the heater elements 260 may extend along a substantial entire length (e.g., in the X-direction) of the arc portion 206.

The heater elements 260 may each comprise, for example, a resistive heater. For example, the heater elements 260 may each comprise a strip heater, a ribbon heater, a cartridge heater, a tubular heater, a band heater, a wire element heater, an open coil heater, a flexible heater, or another type of heating element. The heater elements 260 may include, for example, a nickel alloy (e.g., NiCr, FeCrAl, CuNi), a molybdenum alloy, a stainless steel alloy, a tungsten alloy, a ceramic material (e.g., $MoSi_2$, SiC, graphite), or another material, without limitation.

The radiation detector 200 may include one or more temperature sensors 262 for providing an indication of a temperature of one or more portions of radiation detector 200. The temperature sensors 262 may be arranged to measure the temperature of one or more portions of the radiation detector 200, such as the temperature of the facets 230 or temperatures in proximity thereto. In some embodiments, the temperature sensors 262 are located within cavities formed within the facets 230 or within the arc portion 206.

The detector modules 240 in direct physical and thermal contact with the facets 230 may be heated and cooled by the facets 230 which are, in turn, in thermal contact with the heating elements 260 and the heat exchanger 245 (e.g., the fins 252). Accordingly, the temperature of the arc portion 206 may be controlled with the heater elements 260 and the fins 252. In some embodiments, the temperature of the detector modules 240 is indirectly controlled by thermal transfer between the detector modules 240 and the facets 230. Accordingly, the arc portion 206 including the facets 230 to which the detector modules 240 are directly coupled, facilitates improved temperature control of the detector modules 240 and the radiation detector 200.

The temperature of the radiation detector 200 (e.g., one or more of the detector modules 240, the support structure 202, the facets 230, and the arc portion 206) may be controlled with a temperature control system. For example, one or more of the temperature sensors 262 may be electrically coupled to a controller. The controller may be operably coupled to one or more fans 290 for directing air through the volume and across the fins 252 and may also be operably coupled to one or more of the heater elements 260. The fans 290 and the heater elements 260 may be in electrical communication with the controller through one or more electronic boards. The controller may be configured to control the temperature of the detector modules 240 by adjusting one or both of the flow of air through the fins 252 and the power to the heater elements 260 via one or more control signals (not shown). In one or more embodiments, temperature may be controlled in response to a control loop of controller executing a control algorithm or control law known to a person having ordinary skill in the art.

With reference to FIG. 2A and FIG. 2E, in use and operation, the radiation detector 200 may include a cover 292 configured to be coupled to the support structure 202. The cover 292 may be configured to enclose the cavity 255 such that during use and operation, the flow of air through the cavity 255 and across the fins 252 is independent of the rotation speed of the radiation detector 200. In some embodiments, the fans 290 are coupled to the cover 292. In some embodiments, the support structure 202 includes apertures 294 for receiving fasteners for coupling the cover 292 to the support structure 202.

With reference to FIG. 2F, in some embodiments, the radiation detector 200 includes a top cover 295 configured to be operably coupled to the support structure 202. The top cover 295 may be transparent to the radiation 250. With reference to FIG. 2A, in some embodiments, the radiation detector 200 includes shielding materials 296 configured to shield the radiation 250 from undesired portions of the radiation detector 200. In some embodiments, the shielding material 296 comprise tungsten. In some embodiments, a shielding material 270 may be located within the spaces 232 between neighboring facets 230. In some embodiments, the shielding material 270 comprises tungsten.

As described above, the radiation detector 200 may include one or more electronic boards to facilitate operation of the detector modules 240 and the scanning system 100 (FIG. 1) and more specifically, to facilitate electrical communication between the detector modules 240 and the radiation detector 200. Electronics of the electronic boards may be configured to control the radiation detector 200 and the rotor 106 (FIG. 1). In some embodiments, the electronic boards may be configured to distribute power throughout the scanning system 100 (FIG. 1) and signals to and from, for example, the rotor 106 and other components of the scanning system 100 and the radiation detector 200.

Although the radiation detector 200 has been described and illustrated as including a heat exchanger 245 including the fans 290 and the fins 252, the disclosure is not so limited. In other embodiments, the heat exchanger 245 configured for cooling the temperature of the arc portion 206 and the detector modules 240 may include other structures. For example, the heat exchanger 245 may include a cooling structure including a chiller or a water cooler. In some such embodiments, the cavity 255 may not include the fins 252 and may include a chiller including, for example, pipes through which cooling water flows to control a temperature of the arc portion 206 with water cooling. In some embodiments, the arc portion 206 is in thermal communication with a structure including pipes or channels through which water may be flowed to control a temperature thereof. By way of non-limiting example, the cavity 255 may not include the fins 252 but may include a structure interfacing with a lower portion of the arc portion 206 and including channels configured to flow water therethrough. A temperature of the structure and the temperature of the arc portion 206 may be controlled based on one or both of the temperature of a fluid (e.g., water) flowing through the channel, a flow rate of the fluid, a surface area of the channel, and a volume of the channel. In some embodiments, the cavity 255 is replaced with a solid material including one or more channels therein. In other embodiments, at least a portion of the arc portion 206 may include pipes through which water may be flowed to control a temperature of the arc portion 206.

Figure 3:
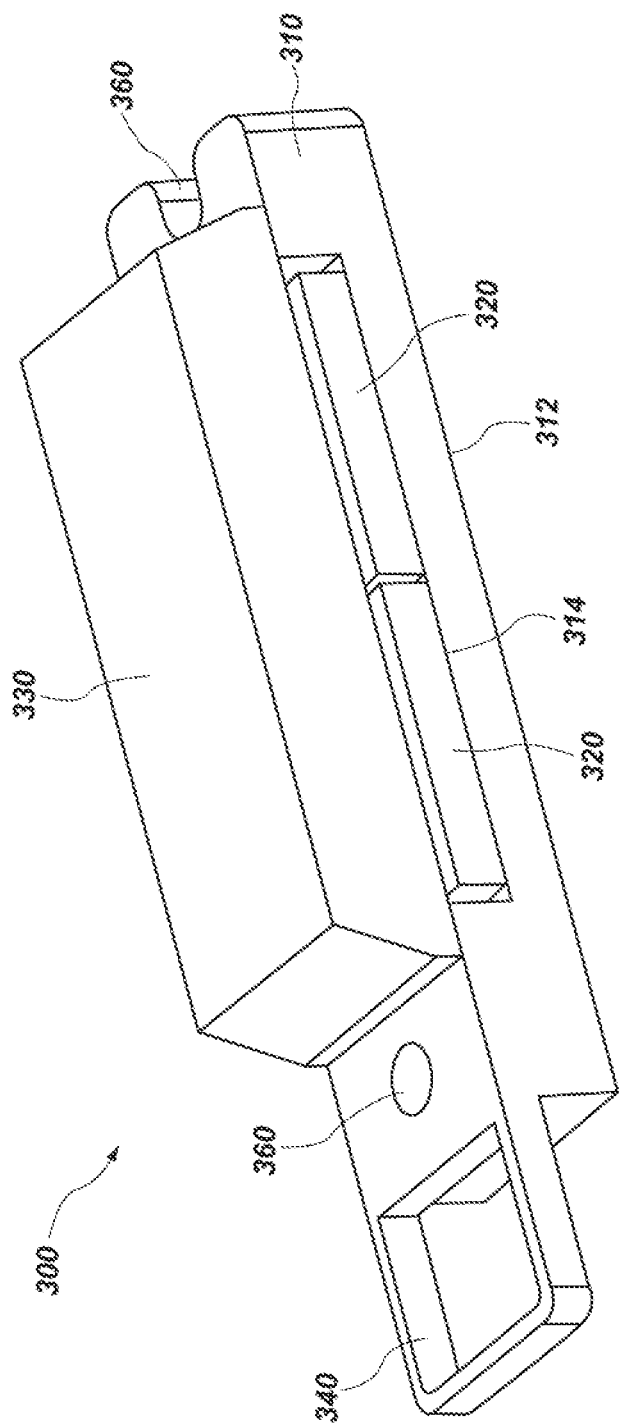
FIG. 3 is a simplified perspective view a detector module, in accordance with embodiments of the disclosure.

FIG. 3 is a simplified perspective view of a detector module 300, in accordance with embodiments of the disclosure. The detector module 300 may include the detector module 240 of FIG. 2A. The detector module 300 may include a base structure 310 including a first surface 312 and a second surface 314 opposite the first surface 312, one or more detector units 320 overlying the base structure 310, and an anti-scatter module (ASM) 330 overlying the detector units 320. The detector module 300 may further include a handle 340 operably coupled to the base structure 310. Each detector unit 320 may be referred to herein as a "detector tile" or simply as a "tile." The anti-scatter module may absorb undesired radiation that has been scattered by the object (e.g., object 102 (FIG. 1)) being scanned.

The detector module 300 may include one or more connectors for electrically connecting the detector module 300 to the radiation detector 200 (e.g., such as to an electronic board of the radiation detector 200).

The detector module 300 may include apertures 360 or cutout portions that correspond to the spacing and location of the apertures 234 (FIG. 2C) of the facets 230 (FIG. 2C). In some embodiments, the detector module 300 may be attached to the surface 236 of the facet 230 by aligning the apertures 360 with the apertures 234 of a corresponding facet 230 and securing the detector module 300 to the corresponding facet 230 with fastening means (e.g., bolts, screws, other structures).

Surfaces of the detector units 320 may directly contact the second surface 314 of the base structure 310. The detector units 320 may be in direct thermal contact with the second surface 314 of the base structure 310. In some embodiments, the first surface 312 may be substantially planar and may contact the surface 236 of a corresponding facet 230 and the second surface 314 may be substantially planar and parallel to the first surface 312 and may be configured to receive one or more detector units 320.

Figure 4A:
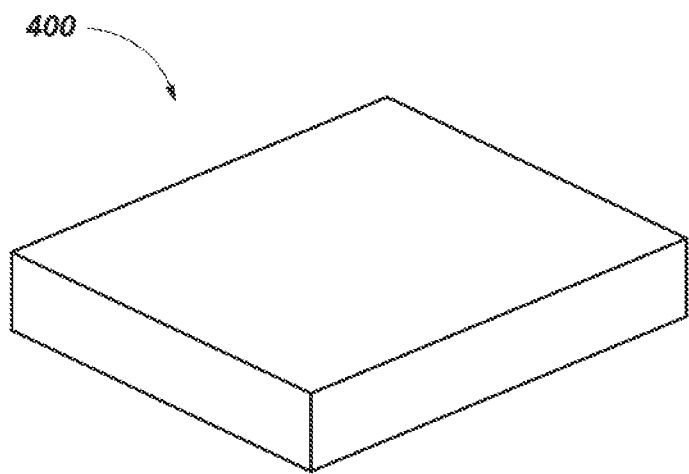
FIG. 4A and FIG. 4B are simplified perspective views of a detector unit, in accordance with embodiments of the disclosure.
Figure 4B:
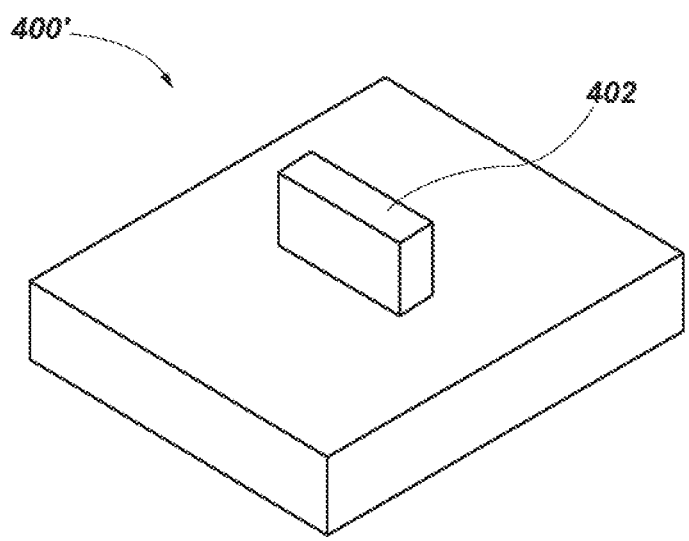

FIG. 4A is a simplified perspective view of a detector unit 400 (e.g., an indirect conversion detector unit, a direct conversion detector unit), in accordance with embodiments of the disclosure. The detector unit 400 may include, for example, one of detector units 320 (FIG. 3) of the detector module 300 (FIG. 3). FIG. 4B is a simplified perspective view of a detector unit 400' that may correspond to, for example, one of the detector units 320 (FIG. 3), in accordance with embodiments of the disclosure.

The detector units 400, 400' may comprise a detector tile configured to be coupled to the detector module 300 (FIG. 3). With reference to FIG. 4B, in some embodiments, the detector unit 400' includes a connector 402 for electrically coupling the detector unit 400' to the radiation detector 200 (FIG. 2), such as to an electronic board of the radiation detector 200.

The detector units 400, 400' may comprise an indirect conversion detector unit, or a direct conversion detector unit. For example, in some embodiments, the detector units 400, 400' include a photodetector array coupled to a scintillator array, as known in the art. In another embodiment, the detector units 400, 400' include a direct conversion detector such as CzZnTe, as known in the art. In addition, in some embodiments the detector units 400, 400' may include radiation shielding materials formulated and configured to inhibit or attenuate at least some of the radiation photons (e.g., x-ray and/or gamma-ray photons) impingent thereon. By way of non-limiting example, the radiation shielding materials may include one or more of tungsten, lead, tantalum, leaded glass, and heavy metal powder composites (e.g., tungsten powder in a polymer binder). In some embodiments, radiation shielding material comprises tungsten.

In use and operation of the scanning system 100, the detector units 320 (e.g., detector units 400, 400') of the detector module 300 generate heat. As the size of the scanning system 100 (and the corresponding size of the radiation detector 116) increases, the size of the detector modules 240, 300 and/or number of the detector units 320 may exhibit a corresponding increase. The heat generated by the detector units 320 may be removed from the radiation detector 116 by means of the support structure 202 including the arc portion 206. For example, heat from the detector units 320 may be transferred from the detector units 320 to the first surface 312 of the base structure 310 and from the base structure 310 directly to the facets 230 of the arc portion 206. Heat may be transferred through the arc portion 206 and may be removed from the system through the fins 252, such as by flowing air through the fins 252 or through a cooling medium (e.g., cooling water), as described above.

The radiation detector 200 according to embodiments of the disclosure may facilitate improved accuracy of images generated with the scanning system 100 (FIG. 1). For example, the facets 230 may substantially completely support the detector modules 240, 300, reducing or substantially preventing deflection of the detector modules 240 and the associated detector units (e.g., the detector units 320). Stated another way, the base structure 310 of the detector modules 240, 300 may be fully supported on the surface 236 of the facets 230 and the detector units 320 may be fully supported on the second surface 314 of the base structure 310. Accordingly, during rotation of the rotor 106 (FIG. 1) and accompanying the radiation detector 116 (FIG. 1), the G-forces exerted on the detector modules 240, 300 may not substantially deflect the detector module 240, 300 including the detector units 320 since the base structure 310 is supported by the facets 230. By way of comparison, detector units of conventional scanning systems are not fully supported by a facet or other supporting structure. For example, detector units of so-called "spine" type cradles include a mounting bracket comprising a first surface that is mounted to the cradle that is rotated and a second surface to which the detector units are mounted. The second surface is oriented at a right angle with respect to the first surface. Accordingly, as the rotor rotates, the G-forces on the detector module cause the detector units to bend, reducing the accuracy of measurements made with the detector units. Other types of conventional scanning system include so-called "polygon" type cradles wherein support structures for the detector units are spanned across different portions of the cradle. However, as the rotor rotates, the support structures bend, causing a corresponding bend in the detector units and a reduction in accuracy of the measurements made with the detector units.

In addition, the radiation detector 200 including the including the arc portion 206 according to embodiments of the disclosure may facilitate improved temperature control of the detector modules 240, 300 and the detector units 320 (e.g., the detector units 400, 500) compared to conventional scanning systems. For example, the arc portion 206 facilitates indirect thermal transfer between the detector modules 240 and a surrounding environment through the arc portion 206. The temperature of the arc portion 206 may be controlled by removing heat from the arc portion 206 by means of the fins 252 and the passage of air, and by controlling the power of the heater elements 260. By way of comparison, the temperature of detector modules of conventional scanning systems may be directly controlled by passage of air as the rotor rotates and air is passed across the detector modules. However, such methods may result in inadequate temperature control of the detector module. For example, the rate of heat transfer from the detector modules may be dependent upon the rotation speed of the rotor. Removing heat from the radiation detector 200 through the arc portion 206, as described herein, may facilitate a more uniform temperature control of the radiation detector 200 compared to conventional scanning systems. For example, due to the relatively large thermal mass of the arc portion 206, the rate of temperature change of the arc portion 206 and coupled radiation detectors 200 is substantially slower (e.g., the time constant of temperature change is greater) compared to conventional scanning systems. Accordingly, the scanning systems including the detector array according to embodiments described herein may not be as susceptible to changes in air flow or rotation speed of the rotor compared to conventional scanning systems.

In addition, the second surface 314 of the detector module 300 that contacts the corresponding substantially planar surface 236 of the facet 230 facilitates direct coupling and alignment of the detector module 300 to the facets 230 of the radiation detector 200. In addition, the apertures 360 of the detector module 300 facilitate alignment of the detector module 300 to the flat substantially planar surface 236 of the facets 230. The apertures 360 and the handle 340 of the detector module 300 allow for improved servicing of the radiation detector 200 compared to conventional scanning systems.

Although FIG. 2A through FIG. 2E have been described and illustrated as including the radiation detector 200 comprising the support structure 202 including the arc portion 206 having a particular shape, the disclosure is not so limited. FIG. 5A is a simplified cross-sectional view of a radiation detector 500, in accordance with embodiments of the disclosure. The radiation detector 500 may be substantially similar to the radiation detector 200 of FIG. 2A through FIG. 2F, except that the radiation detector 500 may include a support structure 502 exhibiting a different shape than the support structure 202 of the radiation detector 200. The support structure 502 may exhibit a truncated hexagonal shape. The support structure 502 may be located opposite a radiation source 514 configured to emit radiation 550 toward facets 530 of the support structure 502.

The support structure 502 may define a cavity 555 configured to receive a heat exchanger 545, as described above with reference to the cavity 255 of the support structure 202. In some embodiments, the heat exchanger 545 may comprise fins 552, as described above with reference to the heat exchanger 245. Fans may be coupled to the support structure 502 and configured to provide air through the fins 552, as described above with reference to the fans 290. Accordingly, the support structure 502 may exhibit a truncated hexagonal shape.

Figure 5B:
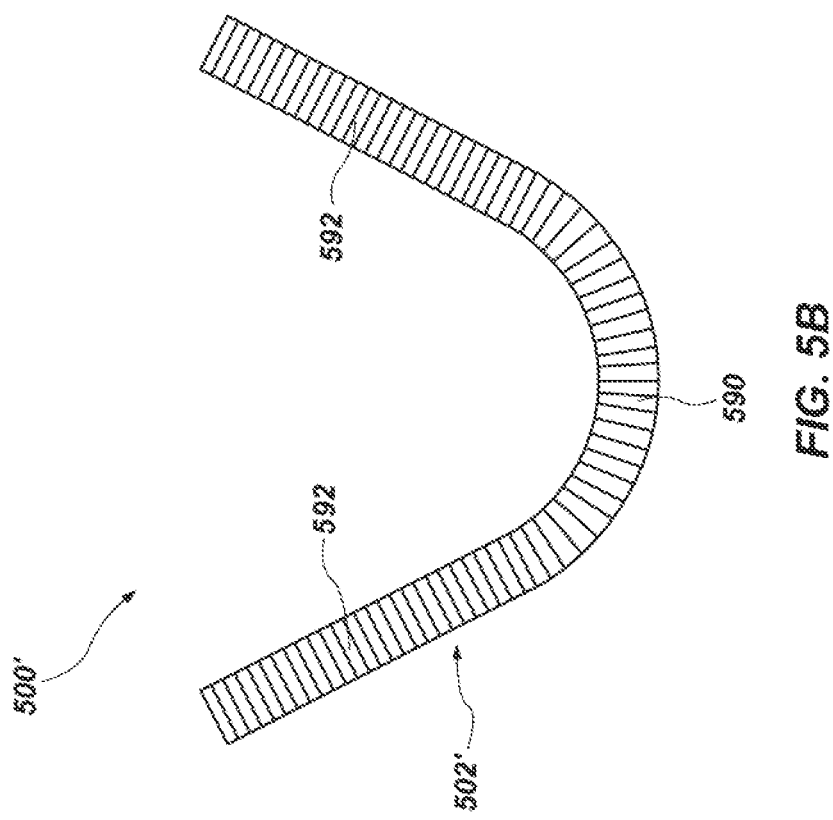
FIG. 5B is a simplified cross-sectional view of a radiation detector, in accordance with other embodiments of the disclosure.
Figure 5A:
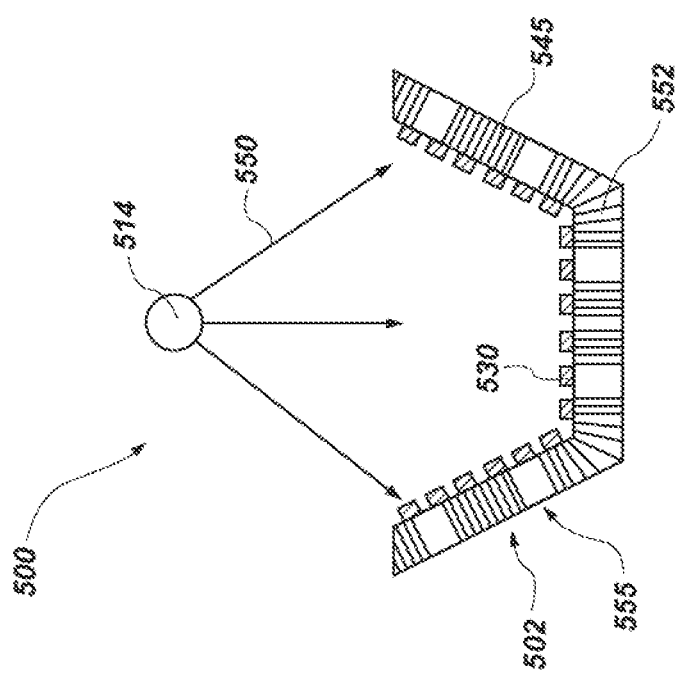
FIG. 5A is a simplified cross-sectional view of a radiation detector, in accordance with embodiments of the disclosure.

FIG. 5B is a simplified cross-sectional view of a radiation detector 500', in accordance with embodiments of the disclosure. The radiation detector 500' may be substantially similar to the radiation detector 500, except that the radiation detector 500' may exhibit a different cross-sectional shape. For example, the radiation detector 500' may include a support structure 502' including a first portion 590 exhibiting a circular shape and second portions 592 coupled to the first portion 590 and exhibiting a substantially linear shape. The support structure 502' may include facets (not shown) as described above with reference to the radiation detector 500 and the radiation detector 200.

Figure 5C:
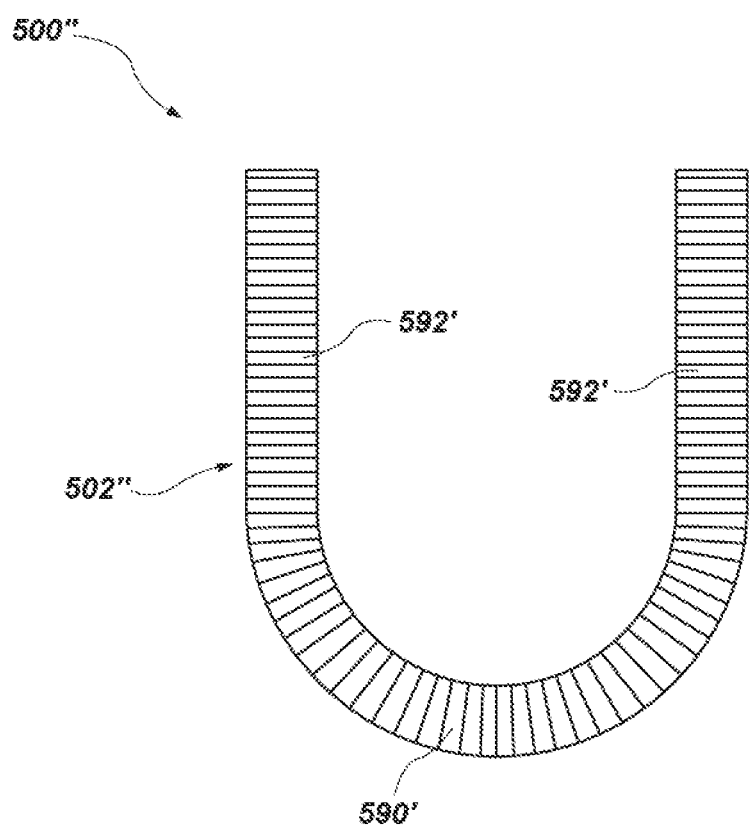
FIG. 5C is a simplified cross-sectional view of a radiation detector, in accordance with additional embodiments of the disclosure.

FIG. 5C is a simplified cross-sectional view of a radiation detector 500", in accordance with embodiments of the disclosure. The radiation detector 500" may be used in an emission system (e.g., a SPECT system, a PET system). The radiation detector 500" may be substantially similar to the radiation detector 500', except that the radiation detector 500" may exhibit a different cross-sectional shape. For example, the radiation detector 500" may include a support structure 502" exhibiting a U-shape. The support structure may include a first portion 590' exhibiting a circular shape and second portions 592' coupled to the first portion 590' and exhibiting a substantially linear shape. An angle between the first portion 590' and the second portions 592' may be different than the angle between the first portion 590 and the second portions 592 of the support structure 502' of FIG. 5B. In some embodiments, the second portions 592' are oriented substantially parallel to one another. The support structure 502" may include facets (not shown) as described above with reference to the radiation detector 500 and the radiation detector 200.

Figure 6:
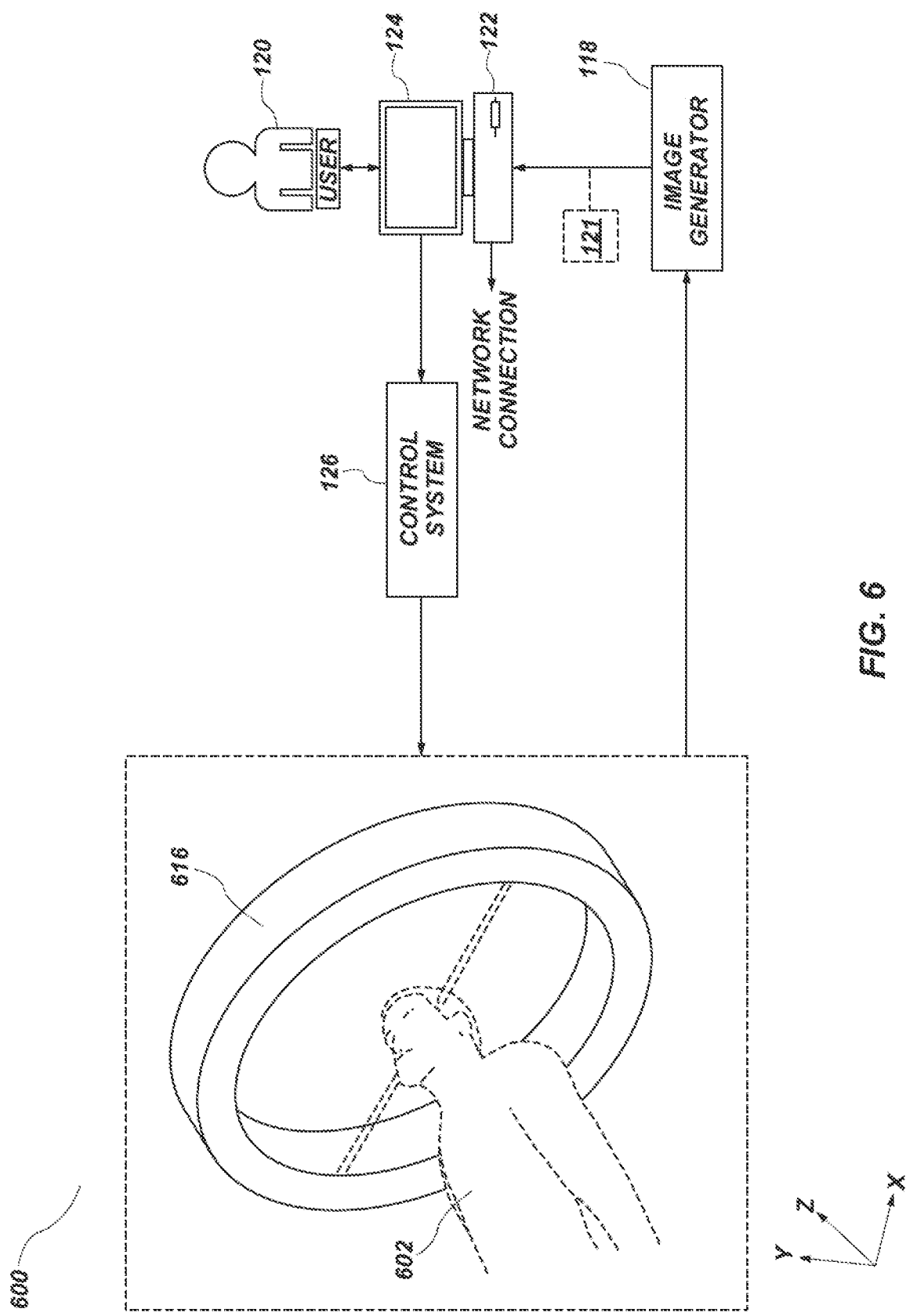
FIG. 6 is a schematic of a scanning system to perform emission radiation-based scanning, in accordance with embodiments of the disclosure.

Although FIG. 1 and FIG. 2A through FIG. 2E have been described and illustrated as comprising a scanning system 100 including a particular type of radiation detector 116, 200, the disclosure is not so limited. In other embodiments, radiation detector 200 may include a so-called position emission tomography (PET) system wherein the radiation detector is in the form of a ring. FIG. 6 is a simplified schematic of a scanning system comprising, for example, a position emission tomography (PET) scanning system 600. PET scanning system 600 may be substantially similar to the scanning system 100 of FIG. 1, except that PET scanning system 600 may include a different radiation detector. The PET scanning system 600 may include a detector array 616 arranged in a ring shape. The detector array 616 may be substantially similar to the radiation detector 116, 200 (FIG. 1. FIG. 2A through FIG. 2F), except that the radiation detector 616 may include detectors arranged around a circumference of substantially all of a circle. In some embodiments, the radiation detector 616 may be formed from segments, such as from one or more radiation detectors 200, 500, 500', 500" arranged to form a circular shape. Accordingly, the radiation detector 616 may include a support structure (e.g., the support structure 202) including an arc portion (e.g., the arc portion 206) arranged around substantially all of a circle. Alternatively, the PET scanning system 600 may include a detector array 616 arranged in a combination of circular and linear sections, such as shown and described with reference to FIG. 5B. In addition, the PET scanning system 600 may not include a radiation source (e.g., the radiation source 114 (FIG. 1)). In some such embodiments, a patient 602 may include (e.g., be injected with) a radioactive tracer material.

Accordingly, radiation detectors according to embodiments described herein may include a support structure including an arc portion configured to be in physical and thermal contact with detector modules placed on facets of the arc portion. The facets and the detector modules may be enclosed within the support structure and may not be in direct fluid communication with an external environment. The arc portion may exhibit a thermal mass relatively larger than a thermal mass of the individual detector modules. The arc portion may be in thermal communication with one or more heater elements and one or more cooling elements (e.g., the fins 252 (FIG. 2A, FIG. 2B)). A temperature of the detector modules may be controlled indirectly through controlling the temperature of the arc portion of the support structure, which may be controlled by operation of the heater elements and the cooling elements. The relatively large thermal mass of the arc portion and the isolation of the detector modules from the external environment may facilitate improved temperature control of the detector modules compared to conventional scanning systems. In addition, the facets may facilitate improved physical support of the detector modules during use and operation, reducing physical deflection and bending of the detector modules compared to conventional scanning system.

While embodiments of the disclosure may be susceptible to various modifications and alternative forms, specific embodiments have been shown by way of example in the drawings and have been described in detail herein. However, it should be understood that the disclosure is not limited to the particular forms disclosed. Rather, the disclosure encompasses all modifications, variations, combinations, and alternatives falling within the scope of the disclosure as defined by the following appended claims and their legal equivalents.

What is claimed is:

1. A radiation scanning system, comprising:
   a radiation detector arranged to receive at least some radiation, the radiation detector comprising:
      an arc portion at least partially defining a circle, the arc portion comprising a unitary body forming a plurality of facets on a side thereof, each facet of the plurality of facets comprising a substantially planar surface tangent to the circle at least partially defined by the arc portion;
      a detector module coupled to the substantially planar surface of each facet of the plurality of facets, the detector module comprising a base portion comprising a first substantially planar surface, the entire first substantially planar surface in contact with the substantially planar surface of a respective facet of the plurality of facets;
      a plurality of detector units coupled to a second substantially planar surface of the base portion and each individually comprising a photodetector array coupled to a scintillator array, surfaces of the detector units of the plurality of detector units coplanar with each other, the second substantially planar surface parallel with the first substantially planar surface; and
      a heat exchanger for removing heat from the arc portion in thermal communication with a side of the arc portion opposite the plurality of facets.

2. The radiation scanning system of claim 1, wherein the heat exchanger comprises fins vertically below and within horizontal boundaries of the plurality of facets.

3. The radiation scanning system of claim 1, wherein the heat exchanger comprises a water chiller.

4. The radiation scanning system of claim 1, wherein the plurality of facets are oriented to face a radiation source.

5. The radiation scanning system of claim 1, further comprising a shielding material between neighboring facets.

6. The radiation scanning system of claim 1, wherein a surface of each detector module is oriented substantially perpendicular to a line between the surface of the respective detector module and a radiation source.

7. The radiation scanning system of claim 1, wherein each detector unit comprises an indirect conversion detector unit.

8. The radiation scanning system of claim 1, wherein each detector unit comprises a handle operably coupled to the base portion.

9. The radiation scanning system of claim 1, further comprising one or more resistive heater elements in thermal communication with the arc portion.

10. A radiation detector for a radiation imaging system, the radiation detector comprising:
    an integral support structure comprising:
       a base portion; and
       an arc portion spaced from the base portion, the arc portion comprising a first surface comprising a plurality of facets facing a center of a circular shape at least partially defined by the arc portion and a second surface opposite the first surface, each facet of the plurality of facets comprising apertures;
    a cooling structure at least partially located between the base portion and the arc portion; and
    a detector module coupled to each facet of the plurality of facets with fasteners extending through the apertures of a respective facet of the plurality of facets and corresponding apertures of the detector module, each facet of the plurality of facets in direct thermal communication with a respective detector module, each detector module comprising a detector unit.

11. The radiation detector of claim 10, further comprising a cover transparent to radiation enclosing the cooling structure from an external environment, the cover between a radiation source and the detector modules.

12. The radiation detector of claim 10, wherein a surface of each detector module faces a direction of a radiation source.

13. The radiation detector of claim 10, wherein each detector module comprises a substantially planar surface.

14. The radiation detector of claim 10, wherein the cooling structure comprises a plurality of fins and one or more fans.

15. The radiation detector of claim 10, wherein the cooling structure comprises a water cooler.

16. The radiation detector of claim 10, further comprising a heater element adjacent to the second surface.

17. A radiation system, comprising:
a radiation detector, comprising:
- a plurality of detector modules arranged on an arc portion of a cradle configured to rotate around a detection area, the arc portion comprising a continuous surface comprising a plurality of facets, each detector module comprising apertures and a detector unit having a major surface substantially perpendicular to a line extending from the major surface to a center of a circle defined at least partially by the arc portion, each detector module coupled to a respective facet of the plurality of facets with fasteners extending through apertures of the respective facet and the apertures of the detector module; and
- a cooling structure on a side of the arc portion opposite the plurality of detector modules and configured to transfer heat from the arc portion, the cooling structure comprising a plurality of fins within a cavity directly vertically below the plurality of detector modules and within horizontal boundaries of the arc portion.

18. The radiation system of claim 17, wherein the major surface of each detector unit is exposed in a direction toward a radiation source.

19. The radiation system of claim 17, further comprising one or more heater elements on the side of the arc portion opposite the plurality of detector modules, the one or more heater elements closer to the plurality of detector modules than the cooling structure.

20. The radiation system of claim 17, wherein the cooling structure comprises cooling fins and one or more fans configured to direct air substantially perpendicular to a length of the arc portion.

21. A radiation scanning system, comprising:
a rotor;
a radiation source coupled to the rotor; and
a radiation detector coupled to the rotor opposite the radiation source, the radiation detector comprising:
- an arc portion comprising a unitary body forming a plurality of facets on a first side thereof;
- a detector module coupled to each facet of the plurality of facets, each detector module individually comprising:
  - a base structure comprising a first substantially planar surface, the entire first substantially planar surface in contact with a respective facet;
  - a handle operably coupled to the base structure; and
  - a plurality of detector units on a second substantially planar surface of the base structure, the second substantially planar surface opposing the first substantially planar surface, each detector unit comprising a photodetector array coupled to a scintillator array, surfaces of each detector unit in contact with the second substantially planar surface and coplanar with surfaces of the other detector units of the plurality of detector units; and
- a cooling structure in thermal communication with a second side of the arc portion.

22. The radiation scanning system of claim 21, wherein the base structure comprises a recessed portion, the plurality of detector units located within the recessed portion.

23. The radiation scanning system of claim 21, wherein each facet of the plurality of facets are separated from each other by spaces.

* * * * *